(12) United States Patent
Reekie et al.

(10) Patent No.: US 10,807,931 B2
(45) Date of Patent: Oct. 20, 2020

(54) SYNTHESIS OF PHYTOCANNABINOIDS INCLUDING A DECARBOXYLATION STEP

(71) Applicant: THE UNIVERSITY OF SYDNEY, New South Wales (AU)

(72) Inventors: Tristan Reekie, New South Wales (AU); Michael Scott, New South Wales (AU); Michael Kassiou, New South Wales (AU)

(73) Assignee: THE UNIVERSITY OF SYDNEY, Sydney (AU)

( * ) Notice: Subject to any disclaimer, the term of this patent is extended or adjusted under 35 U.S.C. 154(b) by 0 days.

(21) Appl. No.: 16/639,202

(22) PCT Filed: Aug. 16, 2018

(86) PCT No.: PCT/AU2018/050870
§ 371 (c)(1),
(2) Date: Feb. 14, 2020

(87) PCT Pub. No.: WO2019/033168
PCT Pub. Date: Feb. 21, 2019

(65) Prior Publication Data
US 2020/0172459 A1 Jun. 4, 2020

(30) Foreign Application Priority Data
Aug. 16, 2017 (AU) .................. 2017903287

(51) Int. Cl.
*C07C 37/50* (2006.01)
*C07C 39/15* (2006.01)
*C07D 311/58* (2006.01)
*C07D 311/80* (2006.01)
*C07D 311/94* (2006.01)

(52) U.S. Cl.
CPC .............. *C07C 37/50* (2013.01); *C07C 39/15* (2013.01); *C07D 311/58* (2013.01); *C07D 311/80* (2013.01); *C07D 311/94* (2013.01)

(58) Field of Classification Search
CPC ....... C07C 37/50; C07C 39/15; C07D 311/58; C07D 311/80; C07D 311/94
See application file for complete search history.

(56) References Cited

U.S. PATENT DOCUMENTS 4,066,674 A 1/1978 Eder et al.
2010/0298579 A1 11/2010 Steup et al.

FOREIGN PATENT DOCUMENTS

WO WO-2007/041167 A2 4/2007

OTHER PUBLICATIONS

Hurd & Shah, Decarboxylation Studies on 3,5-Dihydroxyhomophthalic Acid Derivatives, 38(3) J. Org. Chem. 610-612 (1973) (Year: 1973).*
Buchi et al., Total syntheses of atrovenetin and Scleroderodione, J. Org. Chem., 51:4813-8 (1986).
Covarrubias-Zuniga et al., A total synthesis of the antibiotic DB-2073, Synthetic Communications, 33(18):3173-81 (2003).
Hurd et al., Decarboxylation studies on 3,5-Dihydroxyhomophthalic acid derivatives, J. Org. Chem., 38:610-2 (1973).
International Application No. PCT/AU2018/050870, International Search Report and Written Opinion, dated Sep. 14, 2018.

* cited by examiner

*Primary Examiner* — Timothy R Rozof
(74) *Attorney, Agent, or Firm* — Marshall, Gerstein & Borun LLP

(57) ABSTRACT

Method for decarboxylating a carboxylated phytocannabinoid compound of Formula I to form a phytocannabinoid compound of Formula II: Formula I Formula II wherein: R1 is selected from the group consisting of: substituted or unsubstituted $C_1$-$C_5$ alkyl; R2 is selected from the group consisting of: OH or O, and R3 is selected from the group consisting of: a substituted or unsubstituted cyclohexene, a substituted or unsubstituted $C_2$-$C_8$ alkene, or a substituted or unsubstituted $C_2$-$C_8$ dialkene; or R2 is O, and R2 and R3 together form a ring structure in which R2 is an internal ring atom; wherein the method includes heating a reaction mixture comprising the carboxylated phytocannabinoid compound and a polar aprotic solvent in the presence of a LiCl for a time sufficient to decarboxylate at least a portion of the carboxylated phytocannabinoid compounds and form the phytocannabinoid compound.

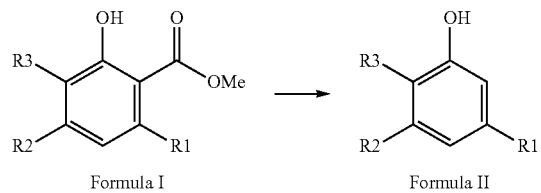

Formula I          Formula II

17 Claims, No Drawings

SYNTHESIS OF PHYTOCANNABINOIDS INCLUDING A DECARBOXYLATION STEP

FIELD OF THE INVENTION

The present invention relates to methods for the synthesis of phytocannabinoids.

BACKGROUND OF THE INVENTION

Cannabis has been used in traditional medicine for thousands of years and was first introduced to Western medicine in the 1830's. Initial uses were claimed for its analgesic, sedative, anti-inflammatory, antispasmodic and anticonvulsant effects. Over 100 years later, with concerns over its safety, cannabis moved from being listed as a drug used for medical treatment, to narcotic drug, before, in 1970 in the US, being classed as Schedule I drug meaning it had no accepted medicinal use.

Despite being classed as a scheduled narcotic, cannabis was still investigated for its neurobiology, which led to the discovery of the endocannabinoid system (ECS) in 1988, identifying the cannabinoid receptor 1 (CB1) and CB2 five years later. CB1 is concentrated in the central nervous system (CNS) while CB2 is found predominately in the periphery giving rise to different functions. CB1 modulates mood, appetite, memory and pain whereas CB2 is associated with a role in immunity.

Phytocannabinoids exist as six main structural classes; tetrahydrocannabinol (THC), cannabidiol (CBD), cannabigerol (CBG), cannabichromene (CBC), cannabicyclol (CBL) and cannabinol (CBN). When a carboxylic acid is incorporated on the aromatic between the phenol and aliphatic chain then a suffix of A is included, while a propyl versus pentyl chain gets the suffix V, or a combination of both suffixes. Quantities of each class available from extracts depends on the species of plant, growing conditions and location, method of extraction and whether it was leaves, buds, stems or roots and in which point in growth they were extracted.

Phytocannabinoids have returned to the pharmacy in the form of dronabinol, an orally taken capsule comprising THC as the active ingredient, and nabiximols (Sativex) a mouth spray comprising a 1:1 mixture of THC and CBD. Studies surrounding these two drugs have shown the vastly different outcomes achieved when single compounds or a formulation of multiple natural products are employed. Considering these observations, it seems likely that the way forward for cannabis is various formulations of active ingredients combined in such a way that the desired effects are achieved. Full testing of individual components would be required. Plant extracts are limited in that some active ingredients are only available in small quantities or change structure during isolation so that getting sufficient quantities for testing, let alone drug formulation, is minimal. Therefore, fully- or semi-synthetic methodology are required to provide quantities of these compounds for testing, as individual active ingredients, or increasing active ingredient ratios from extracts for ideal drug formulation. However, synthetic protocols are also limited with very little reported for most compounds, and in those cases where methods are reported, only afford the target compounds in very small amounts. Furthermore, presently there are no reported methods for the synthesis of the majority of phytocannabinoids. Those few that are reported are not useful for large scale applications.

It is an object of the invention to address and/or ameliorate at least one of the problems of the prior art.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In a first aspect of the invention, there is provided a method for decarboxylating a carboxylated phytocannabinoid compound of Formula I to form a phytocannabinoid compound of Formula II:

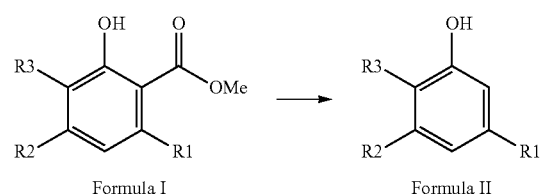

wherein:

R1 is selected from the group consisting of: substituted or unsubstituted $C_1$-$C_5$ alkyl;

R2 is selected from the group consisting of: OH or O, and R3 is selected from the group consisting of: a substituted or unsubstituted cyclohexene, a substituted or unsubstituted $C_2$-$C_8$ alkene, or a substituted or unsubstituted $C_2$-$C_8$ dialkene; or R2 is O, and R2 and R3 together form a ring structure in which R2 is an internal ring atom;

wherein the method includes heating a reaction mixture comprising the carboxylated phytocannabinoid compound and a polar aprotic solvent in the presence of a LiCl for a time sufficient to decarboxylate at least a portion of the carboxylated phytocannabinoid compounds and form the phytocannabinoid compound.

In a second aspect of the invention, there is provided a method for the preparation of a phytocannabinoid compound of Formula II comprising:

subjecting a first reaction mixture comprising a compound of Formula A and a compound of Formula B in a solvent to reaction conditions such that the compound of Formula A and Formula B together undergo a condensation reaction according to Reaction Scheme I to form a carboxulated phytocannabinoid compound of Formula I:

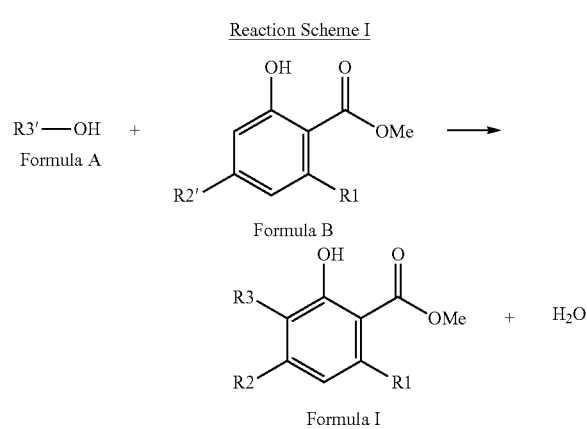

wherein:

R1 is selected from the group consisting of: unsubstituted $C_1$-$C_5$ alkyl;

R2' is OH

R3' is selected from the group consisting of: a substituted or unsubstituted cyclohexene, a substituted or unsubstituted $C_2$-$C_8$ alkene, or a substituted or unsubstituted $C_2$-$C_8$ dialkene R2 is R2' and R3 is R3'; or R2 is O and R2 and R3 together form a ring structure in which R2 is an internal ring atom wherein the method further includes heating a second reaction mixture comprising the carboxylated phytocannabinoid compound and a polar aprotic solvent in the presence of LiCl for a time sufficient to decarboxylate at least a portion of the carboxylated phytocannabinoid compounds and form the phytocannabinoid compound according to Reaction Scheme II;

Reaction Scheme II

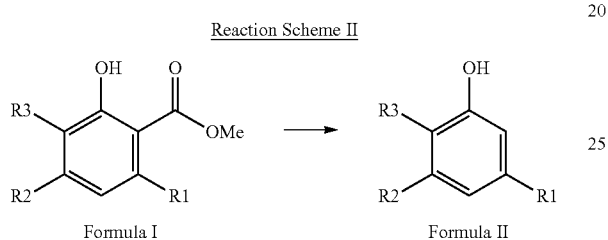

Formula I          Formula II

In an embodiment of the second aspect, the reaction conditions include a sub-zero temperature of around −10° C. or lower (while being above the freezing point of the solvent in the first reaction mixture), such as −10° C. to −30° C. Preferably, the temperature is −15° C. or lower. More preferably, the temperature is about −20° C.

In an embodiment of the second aspect, the first reaction mixture further comprises $BF_3.OEt_2$. Preferably, the $BF_3.OEt_2$ is present in an amount of from about 0.05 molar equivalents (relative to the compound of Formula B) to about 0.50 molar equivalents. More preferably, the $BF_3.OEt_2$ is present in an amount of from about 0.07 molar equivalents to about 0.45 molar equivalents.

In one form of the above embodiment, the $BF_3.OEt_2$ is present in an amount of from about 0.05 molar equivalents to 0.25 molar equivalents. Preferably the $BF_3.OEt_2$ is present in an amount of from about 0.07 molar equivalents to about 0.20 molar equivalents. Most preferably, the $BF_3.OEt_2$ is present in an amount of about 0.10 molar equivalents. The inventors have found that using an amount of $BF_3.OEt_2$ within this range is conducive to the formation of a compound in which R2 and R3 are R2' and R3'. In this form of the invention, the method can further include treating the compound of Formula II with an additional amount of $BF_3.OEt_2$ and warming the first reaction mixture from the sub-zero temperature to form a compound according to Formula II in which R2 is O and R2 and R3 together form a ring structure in which R2 is an internal ring atom. Preferably, during this step, the reaction mixture is warmed from a sub-zero temperature to about 00° C. It is also preferred that the additional amount of $BF_3.OEt_2$ is about 0.10 molar equivalents.

In another form of the above embodiment, the $BF_3.OEt_2$ is present in an amount of greater than 0.25 molar equivalents to 0.50 molar equivalents. Preferably the $BF_3.OEt_2$ is present in an amount of from about 0.35 molar equivalents to about 0.45 molar equivalents. Most preferably, the $BF_3.OEt_2$ is present in an amount of about 0.40 molar equivalents. The inventors have found that using an amount of $BF_3.OEt_2$ within this range is conducive to the formation of a compound in which R2 is O and R2 and R3 together form a ring structure in which R2 is an internal ring atom.

In an embodiment of the first or second aspects, the carboxylated phytocannabinoid compound is a compound of Formula IA and the phytocannabinoid compound is a compound of Formula IIA:

Formula IA

Formula IIA wherein:

R2 is OH and R5 is $C(CH_3)=CH_2$, or R2 is O and R5 is $C(CH_2)_2$ and R2 and R5 are linked by a covalent bond; and R4 is selected from the group consisting of: substituted or unsubstituted $C_1$-$C_4$ alkyl, COOH, COO$C_1$-$C_4$ alkyl, O$C_1$-$C_4$ alkyl, CO$C_1$-$C_4$ alkyl, tetrahydropyran, benzyl, paramethoxybenzyl, and OH.

In an embodiment of the first or second aspects, the carboxylated phytocannabinoid compound is a compound of Formula IB and the phytocannabinoid compound is a compound of Formula IIB:

Formula IB

Formula IIB

In an embodiment of the first or second aspects, the carboxylated phytocannabinoid compound is a compound of Formula IC and the phytocannabinoid compound is a compound of Formula IIC:

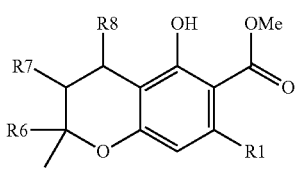

Formula IC

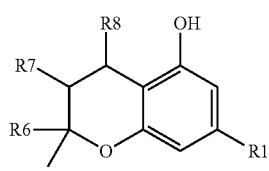

Formula IIC wherein R6 and R7 together form a fused ring structure; R7 and R8 together form a fused ring structure; or R6, R7, and R8 together form a fused ring structure.

In an embodiment of the first or second aspects, the carboxylated phytocannabinoid compound is a compound of Formula ID and the phytocannabinoid compound is a compound of Formula IID:

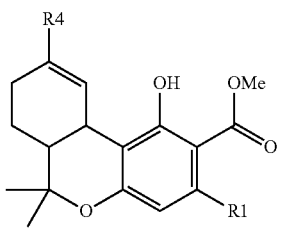

Formula ID

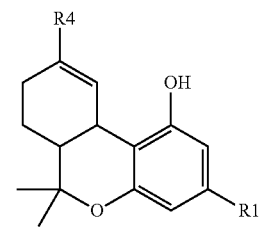

Formula IID

In an embodiment of the first or second aspects, the carboxylated phytocannabinoid compound is a compound of Formula IE and the phytocannabinoid compound is a compound of Formula IIE:

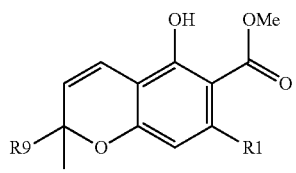

Formula IE

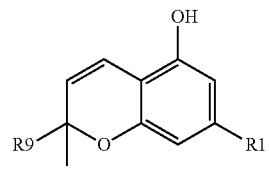

Formula IIE wherein R9 is selected from the group consisting of: a substituted or unsubstituted $C_2$-$C_8$ alkene, or a substituted or unsubstituted $C_2$-$C_8$ dialkene.

In an embodiment the method includes reacting a compound of Formula IF with a compound of the form R9'=O to form a compound of Formula I, wherein R9' is selected from the group consisting of a substituted or unsubstituted $C_5$-$C_{11}$ dialkene:

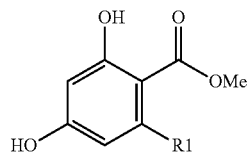

Formula IF wherein the reaction is carried out in the presence of a hydroxide, such as $Ca(OH)_2$.

In a preferred form of this embodiment, the compound of Formula IF is treated with a halocarboxylic acid to form a compound of Formula IC wherein R6, R7, and R8 together form a fused ring structure. Preferably, the halocarboxylic acid is selected from the group consisting of: monochloroacetic acid, dichloroacetic acid, trichloroacetic acid, monobromoacetic acid, dibromoacetic acid, tribromoacetic acid, monofluoroacetic acid, difluoroacetic acid, and trifluoroacetic acid. More preferably, the halocarboxylic acid is trifluoroacetic acid.

In one or more embodiments, R1 is selected from the group consisting of substituted or unsubstituted $C_3$-$C_5$ alkyl. Preferably, R1 is selected from the group consisting of: propyl or pentyl.

In one or more embodiments, R2 is O, and R2 and R3 together form a ring structure, the ring structure is a substituted or unsubstituted six membered heterocyclyl. Preferably the six membered heterocyclyl is a substituted or unsubstituted tetrahydropyran or a substituted or unsubstituted pyranyl.

In one or more embodiments, R4 is selected from substituted or unsubstituted $C_1$-$C_2$ alkyl, COOH, or OH.

In one or more embodiments, R6 and R7 together form a substituted or unsubstituted cyclopentyl.

In one or more embodiments, R7 and R8 together form a substituted or unsubstituted cyclobutyl.

In one or more embodiments, R9 is selected from the group consisting of: a substituted or unsubstituted $C_4$-$C_8$ alkene, or a substituted or unsubstituted $C_4$-$C_8$ dialkene.

In preferred embodiments, the substituents on the substituted moieties is selected from the group selected from —$CH_3$, —$C2H_5$, or —OH.

In an embodiment, the step of heating the reaction mixture includes heating the reaction mixture to the boiling point of the polar aprotic solvent. Preferably, the step of heating the reaction mixture is conducted under reflux.

In an embodiment of the first or second aspects, the step of heating the reaction mixture includes heating the reaction mixture to a temperature such that the reaction proceeds under reflux conditions.

In an embodiment, LiCl is present in an amount of from 1 to 3 molar equivalents (relative to the compound of Formula I). Preferably, the LiCl is present in an amount of from about 1.5 to about 2.5 molar equivalents. Most preferably, the LiCl is present in an amount of about 2 molar equivalents.

In an embodiment of the first or second aspects, the polar aprotic solvent is mixed with up to 10 wt % water. Preferably, the polar aprotic solvent is mixed with up to 5 wt % water.

In an embodiment of the first or second aspects, the polar aprotic solvent is selected from the group consisting of: N-methylpyrrolidone, tetrahydrofuran (THF), ethyl acetate (EtOAc), acetone, dimethylformamide (DMF), acetonitrile (MeCN), dimethyl sulfoxide (DMSO), propylene carbonate (PC), and combinations thereof. Preferably, the polar aprotic solvent is selected from the group consisting of DMSO, DMF, or PC. More preferably, the polar aprotic solvent is DMSO.

In an embodiment, the polar aprotic solvent has a boiling point that is above 100° C. Preferably, the polar aprotic solvent has a boiling point that is above 110° C. More preferably, the polar aprotic solvent has a boiling point that is above 120° C. Even more preferably, the polar aprotic solvent has a boiling point that is above 130° C. Most preferably, the polar aprotic solvent has a boiling point that is above 140° C. Generally, the inventors have found that polar aprotic solvents with higher boiling points are useful as this helps to promote the decarboxylation reaction.

In an embodiment of the first or second aspects, a yield of the phytocannabinoid compound is at least 70% based on the weight of the carboxylated phytocannabinoid compound. Preferably, the yield is at least 75%. More preferably, the yield is at least 80%.

In an embodiment of the first or second aspects, the method further includes separating the phytocannabinoid compound from the polar aprotic solvent.

In an embodiment of the first or second aspects, the phytocannabinoid compound is selected from the group consisting of those listed in Table 1.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

The invention relates to methods of decarboxylating compounds of Formula I to form compounds of Formula II. The invention also more broadly relates to methods of synthesising compounds of Formula I from precursor compounds, and then decarboxylating the compounds of Formula I to form compounds of Formula II.

In view of the above, the invention relates to a method for the preparation of a phytocannabinoid compound of Formula II comprising:

subjecting a first reaction mixture comprising a compound of Formula A and a compound of Formula B in a solvent to reaction conditions such that the compound of Formula A and Formula B together undergo a condensation reaction according to Reaction Scheme I to form a carboxylated phytocannabinoid compound of Formula I:

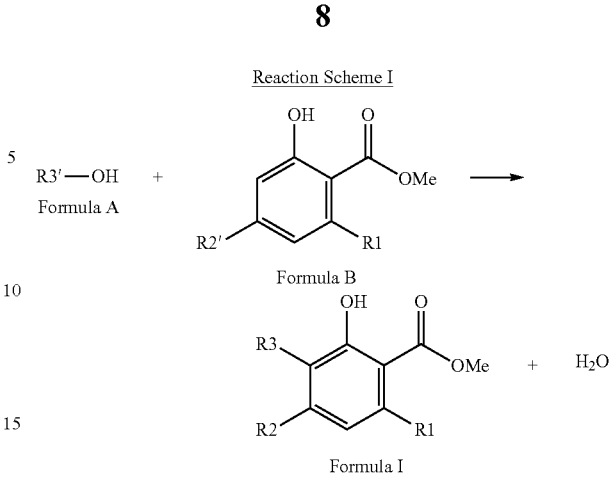

Reaction Scheme I wherein the method further includes heating a second reaction mixture comprising the carboxylated phytocannabinoid compound and a polar aprotic solvent in the presence of LiCl for a time sufficient to decarboxylate at least a portion of the carboxylated phytocannabinoid compounds and form the phytocannabinoid compound according to Reaction Scheme II;

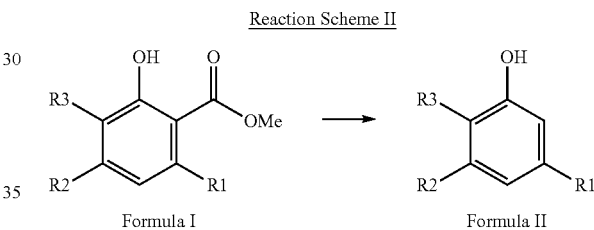

Reaction Scheme II

As used herein, the term "$C_1$-$C_5$ alkyl" either used alone or in compound terms refers to straight chain or branched saturated hydrocarbon groups, having 1 to 4 carbon atoms. Suitable alkyl groups include, but are not limited to: methyl, ethyl, propyl, isopropyl, n-butyl, sec-butyl, tert-butyl. The "$C_1$-$C_5$ alkyl" may be optionally substituted with one or more substituents. The substituents may replace one or more hydrogen atoms on any carbon atom or carbon atoms in the "$C_1$-$C_5$ alkyl" carbon atom chain. Preferred substituents include methyl or ethyl groups, and more preferably methyl groups.

As used herein, the term "$C_2$-$C_8$ alkenyl" either used alone or in compound terms refers to straight chain or branched unsaturated hydrocarbon groups, having 2 to 4 carbon atoms and including at least one carbon to carbon double bond, for example, the alkenyl group may be a monoalkenyl group, a diene group, or a triene group. Suitable alkenyl groups include, but are not limited to: ethenyl, propenyl, propadiene, butenyl, butadiene, pentenyl, pentadiene, hexenyl, hexadiene, heptenyl, heptadiene, octenyl, or octadiene groups. The carbon to carbon double bond may be between any two adjacent carbon atoms. The "$C_2$-$C_8$ alkenyl" may be optionally substituted with one or more substituents. The substituents may replace one or more hydrogen atoms on any carbon atom or carbon atoms in the "$C_2$-$C_8$ alkenyl" carbon atom chain. Preferred substituents include methyl or ethyl groups, and more preferably methyl groups.

The method thus provides a mechanism for preparing a large range of different carboxylated phytocannabinoid compounds from a large range of precursor compounds, which can then be easily decarboxylated to provide an active phytocannabinoid compound. By way of example, the method of invention can be applied to form the phytocannabinoids outlined in Table 1 below:

TABLE 1

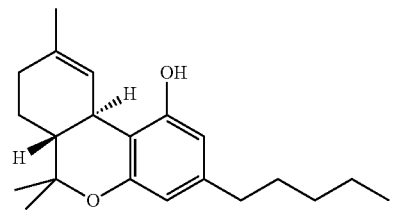 [SMILES: CCCCCc1cc(O)c2c(c1)OC(C)(C)[C@@H]1CCC(C)=C[C@@H]21]

Tetrahydrocannabinol (THC)
(6aR,10aR)-6,6,9-trimethyl-3-pentyl-6a,7,8,10a-tetrahydro-6H-benzo[c]chromen-1-ol

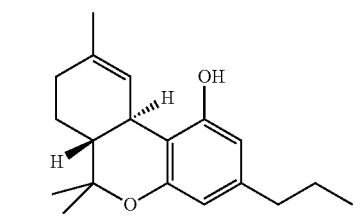 [SMILES: CCCc1cc(O)c2c(c1)OC(C)(C)[C@@H]1CCC(C)=C[C@@H]21]

Tetrahydrocannabivarin (THCV)
(6aR,10aR)-6,6,9-trimethyl-3-propyl-6a,7,8,10a-tetrahydro-6H-benzo[c]chromen-1-ol

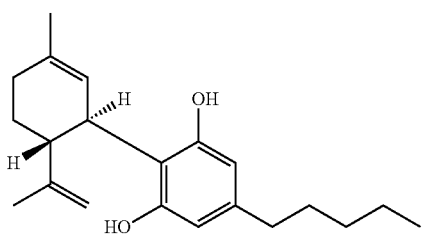 [SMILES: C=C(C)[C@@H]1CCC(C)=C[C@H]1c1c(O)cc(CCCCC)cc1O]

Cannabidiol (CBD)
(1'R,2'R)-5'-methyl-4-pentyl-2'-(prop-1-en-2-yl)-1',2',3',4'-tetrahydro-[1,1'-biphenyl]-2,6-diol

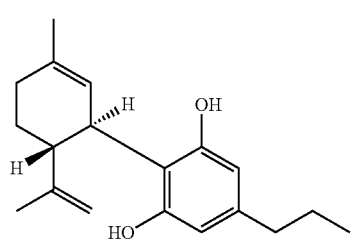 [SMILES: C=C(C)[C@@H]1CCC(C)=C[C@H]1c1c(O)cc(CCC)cc1O]

Cannabidivarin (CBDV)
(1'R,2'R)-5'-methyl-2'-(prop-1-en-2-yl)-4-propyl-1',2',3',4'-tetrahydro-[1,1'-biphenyl]-2,6-diol TABLE 1-continued

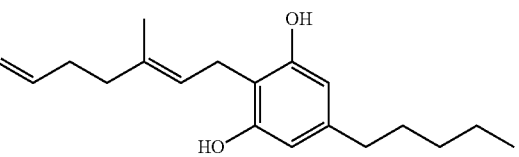

Cannabigerol (CBG)
(E)-2-(3,7-dimethylocta-2,6-dien-1-yl)-5-pentylbenzene-1,3-diol

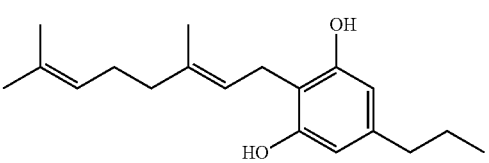 [SMILES: CCCc1cc(O)c(C/C=C(\C)CCC=C(C)C)c(O)c1]

Cannabigerovarin (CBGV)
(E)-2-(3,7-dimethylocta-2,6-dien-1-yl)-5-propylbenzene-1,3-diol

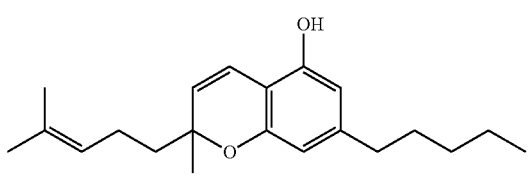 [SMILES: CCCCCc1cc(O)c2c(c1)OC(C)(CCC=C(C)C)C=C2]

Cannabichromene (CBC)
2-methyl-2-(4-methylpent-3-en-1-yl)-7-pentyl-2H-chromen-5-ol

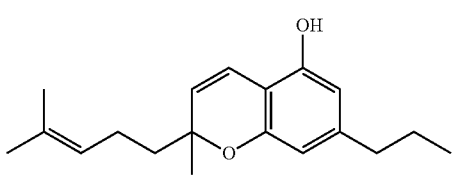 [SMILES: CCCc1cc(O)c2c(c1)OC(C)(CCC=C(C)C)C=C2]

Cannabichromevarin (CBCV)
2-methyl-2-(4-methylpent-3-en-1-yl)-7-propyl-2H-chromen-5-ol

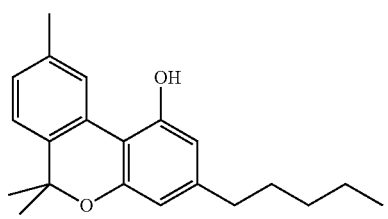 [SMILES: CCCCCc1cc(O)c2c(c1)OC(C)(C)c1ccc(C)cc1-2]

Cannabinol (CBN)
6,6,9-trimethyl-3-pentyl-6H-benzo[c]chromen-1-ol

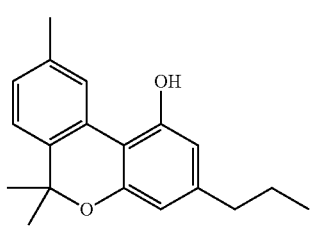 [SMILES: CCCc1cc(O)c2c(c1)OC(C)(C)c1ccc(C)cc1-2]

Cannabinovarin (CBNV)
6,6,9-trimethyl-3-propyl-6H-benzo[c]chromen-1-ol

TABLE 1-continued

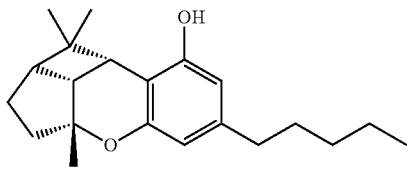

Cannabicyclol (CBL)
(1aS,1a¹R,3aR,8bR)-1,1,3a-trimethyl-6-pentyl-
1a,1a¹,2,3,3a,8b-hexahydro-1H-4-
oxabenzo[f]cyclobuta[cd]inden-8-ol

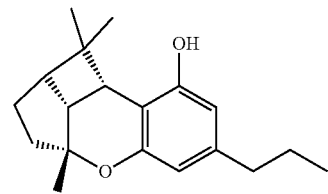

Cannabicyclovarin (CBLV)
(1aS,1a¹R,3aR,8bR)-1,1,3a-trimethyl-6-propyl-
1a,1a¹,2,3,3a,8b-hexahydro-1H-4-
oxabenzo[f]cyclobuta[cd]inden-8-ol

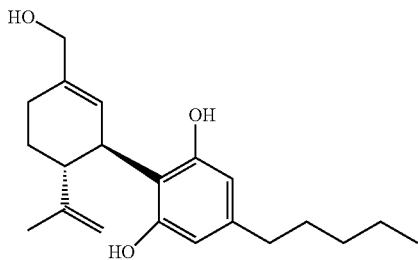 [SMILES: C=C(C)[C@@H]1CCC(CO)=C[C@H]1c1c(O)cc(CCCCC)cc1O]

11-Hydroxycannabidiol (11-OH—CBD)
(1'R,2'R)-5'-(hydroxymethyl)-4-pentyl-2'-(prop-1-en-
2-yl)-1',2',3',4'-tetrahydro-[1,1'-biphenyl]-2,6-diol

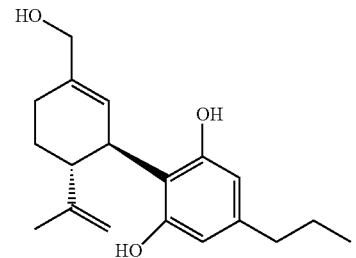 [SMILES: C=C(C)[C@@H]1CCC(CO)=C[C@H]1c1c(O)cc(CCC)cc1O]

11-Hydroxycannabidivarin (11-OH—CBDV)
(1'R,2'R)-5'-(hydroxymethyl)-2'-(prop-1-en-2-yl)-4-
propyl-1',2',3',4'-tetrahydro-[1,1'-biphenyl]-2,6-diol

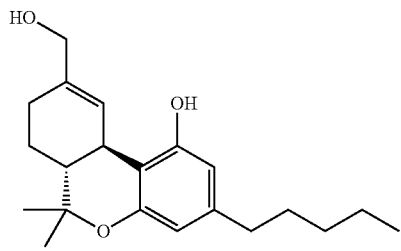 [SMILES: CCCCCc1cc(O)c2c(c1)OC(C)(C)[C@@H]1CCC(CO)=C[C@@H]21]

11-Hydroxytetrahydrocannabinol (11-OH—THC)
(6aR,10aR)-9-(hydroxymethyl)-6,6-dimethyl-3-
pentyl-6a,7,8,10a-tetrahydro-6H-benzo[c]chromen-
1-ol TABLE 1-continued

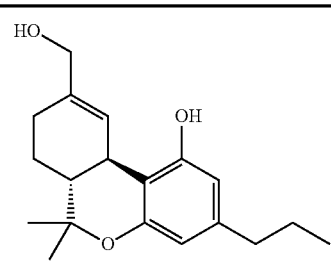

11-Hydroxytetrahydrocannabivarin (11-OH—THCV)
(6aR,10aR)-9-(hydroxymethyl)-6,6-dimethyl-3-
propyl-6a,7,8,10a-tetrahydro-6H-benzo[c]chromen-
1-ol

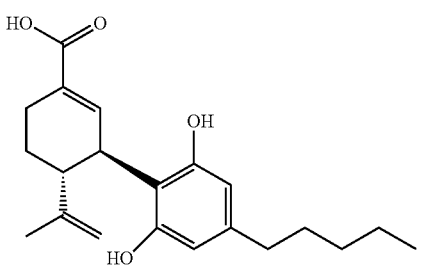 [SMILES: C=C(C)[C@@H]1CCC(C(=O)O)=C[C@H]1c1c(O)cc(CCCCC)cc1O]

11-Carboxycannabidiol (11-COOH—CBD)
(1R,6R)-2',6'-dihydroxy-4'-pentyl-6-(prop-1-en-2-yl)-
1,4,5,6-tetrahydro-[1,1'-biphenyl]-3-carboxylic acid

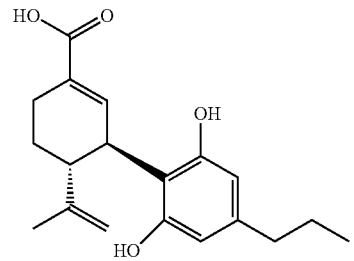 [SMILES: C=C(C)[C@@H]1CCC(C(=O)O)=C[C@H]1c1c(O)cc(CCC)cc1O]

11-Carboxycannabidivarin (11-COOH—CBDV)
(1R,6R)-2',6'-dihydroxy-6-(prop-1-en-2-yl)-4'-propyl-
1,4,5,6-tetrahydro[1,1'-biphenyl]-3-carboxylic acid

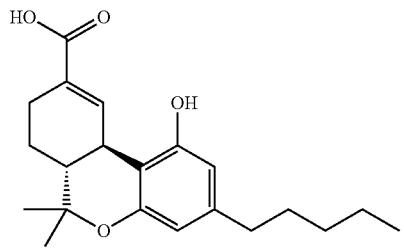 [SMILES: CCCCCc1cc(O)c2c(c1)OC(C)(C)[C@@H]1CCC(C(=O)O)=C[C@@H]21]

11-Carboxytrahydrocannabinol (11-COOH—THC)
(6aR,10aR)-1-hydroxy-6,6-dimethyl-3-pentyl-
6a,7,8,10a-tetrahydro-6H-benzo[c]chromene-9-
carboxylic acid

TABLE 1-continued

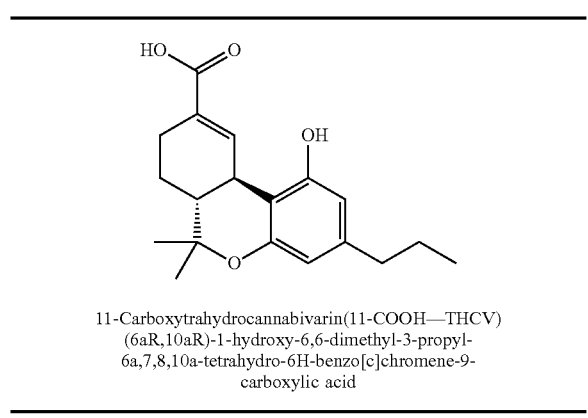

11-Carboxytrahydrocannabivarin(11-COOH—THCV)
(6aR,10aR)-1-hydroxy-6,6-dimethyl-3-propyl-
6a,7,8,10a-tetrahydro-6H-benzo[c]chromene-9-
carboxylic acid

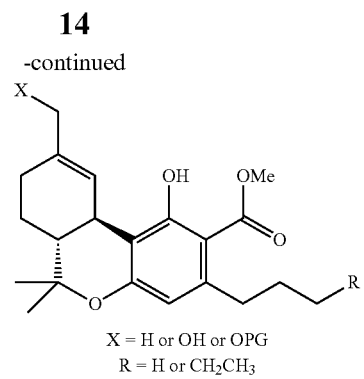

X = H or OH or OPG
R = H or CH₂CH₃

Exemplary reaction schemes are provided below:

Scheme 1

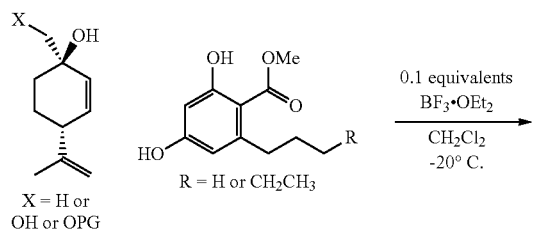

Scheme 3

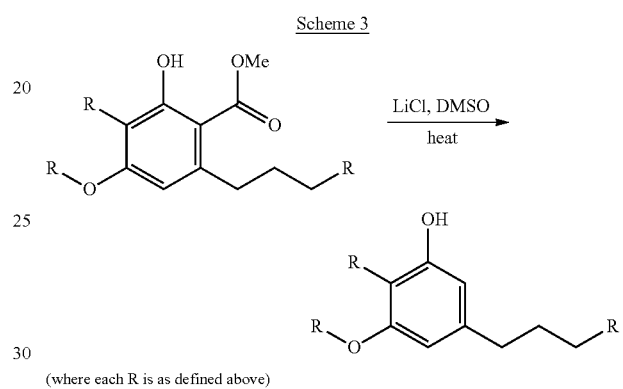

(where each R is as defined above)

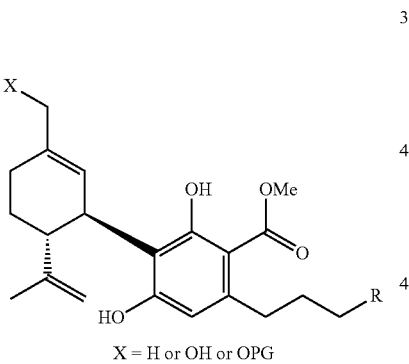

X = H or OH or OPG
R = H or CH₂CH₃

Scheme 4

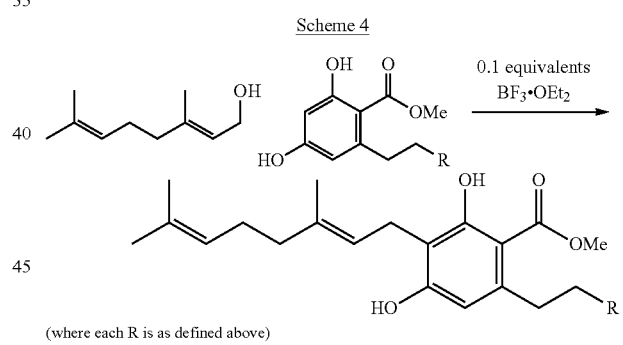

(where each R is as defined above)

Scheme 2

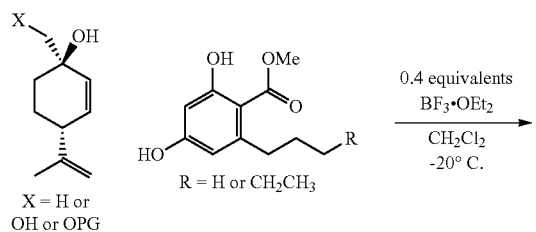

Scheme 5

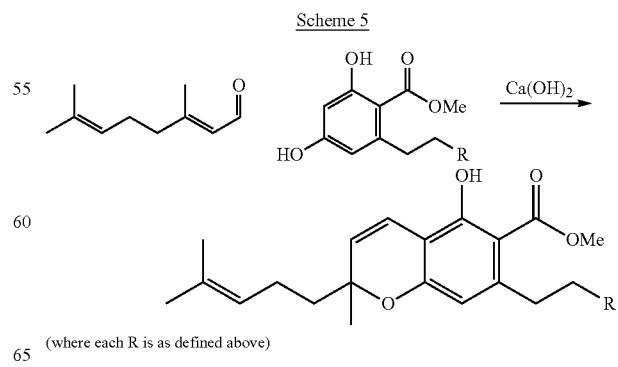

(where each R is as defined above)

Scheme 6

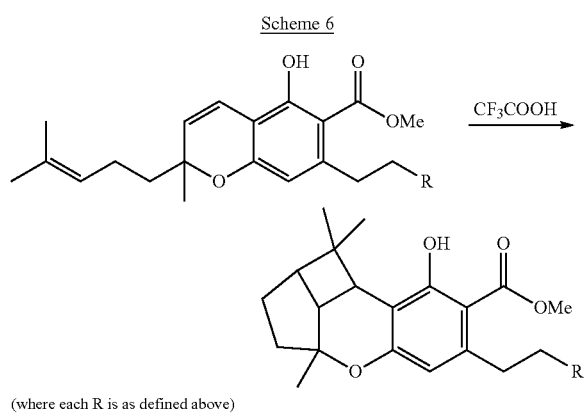

(where each R is as defined above)

EXAMPLES

Example 1—Forming Precursor Compounds of Formula B

Example 1A

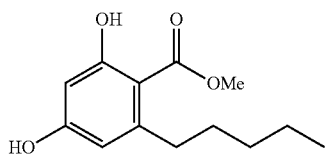 [SMILES: CCCCCc1cc(O)cc(O)c1C(=O)OC]

A solution of methanol (250 mL) at 0° C. was treated with sodium (12.0 g, 0.52 mol) in portions and stirred until dissolved. Dimethyl malonate (67.7 mL, 0.59 mol) was then added followed by (E)-non-3-en-2-one (59 g, 0.42 mol) and the solution heated at reflux for 8 h. The methanol was removed then diluted with water (400 mL) and washed with CHCl$_3$ (300 mL). The aqueous later was acidified and extracted with CHCl$_3$ (3×250 mL). The combined organic layers were dried (MgSO4) and concentrated to give a white solid.

The white solid (8.17 g, 34.0 mmol) was dissolved in DMF (20 ml) and cooled to 0° C. A solution of Br$_2$ (1.75 mL, 34.0 mmol) in DMF (6.6 mL) was slowly added and the solution stirred at 20° C. for 1 h. The solution was then heated to 80° C. for 16 h before cooling and treatment with 5% Na$_2$S$_2$O$_3$ aqueous solution (200 mL) and being extracted with ethyl acetate (3×100 mL). The combined organic layers were dried (MgSO$_4$) and concentrated. The crude material was recrystallized from DCM/hexane to give a white solid.

Example 1B

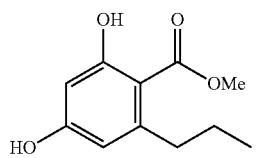

A solution of methanol (450 mL) at 0° C. was treated with sodium (25.5 g, 1.11 mol) in portions and stirred until dissolved. Dimethyl malonate (143 mL, 1.25 mol) was then added followed by (E)-hept-3-en-2-one (100 g, 0.89 mol) and the solution heated at reflux for 8 h. The methanol was removed then diluted with water (600 mL) and washed with CHCl$_3$ (500 mL). The aqueous later was acidified and extracted with CHCl$_3$ (3×400 mL). The combined organic layers were dried (MgSO$_4$) and concentrated to give a white solid.

The white solid (5.37 g, 25.3 mmol) was dissolved in DMF (12 ml) and cooled to 0° C. A solution of Br$_2$ (1.30 mL, 25.4 mmol) in DMF (6.6 mL) was slowly added and the solution stirred at 20° C. for 1 h. The solution was then heated to 80° C. for 16 h before cooling and treatment with 5% Na$_2$S$_2$O$_3$ aqueous solution (200 mL) and being extracted with ethyl acetate (3×100 mL). The combined organic layers were dried (MgSO$_4$) and concentrated. The crude material was recrystallized from DCM/hexane to give a white solid.

Example 2—Forming Compounds of Formula I

Example 2A

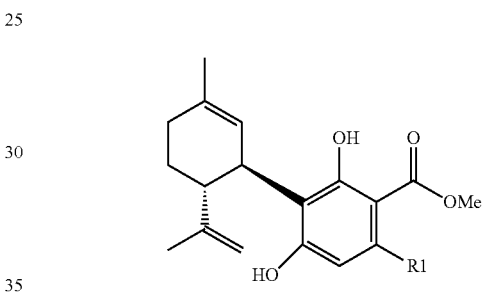

R1 is propyl or pentyl.

A solution of (4R)-1-methyl-4-(prop-1-en-2-yl)cyclohex-2-en-1-ol (1.1 equiv) and methyl 2,4-dihydroxy-6-pentyl-benzoate (1 equiv) or methyl 2,4-dihydroxy-6-propylbenzoate (1 equiv) and MgSO$_4$ (3 equiv) in DCM (0.1 M) at −20° C. was treated with BF$_3$.OEt$_2$ (0.1 equiv) in DCM (0.1 M) and stirred for 0.25 h. Water was added followed and extracted with DCM, dried (MgSO$_4$) and concentrated. The residue was subjected to flash column chromatography (silica, 0 to 5% EtOAc/Hexane gradient elution) to give a colourless oil. Yields 30-40%.

Example 2B

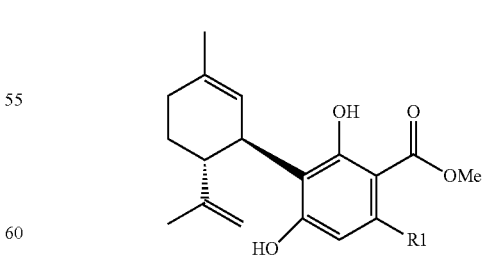

R1 is propyl or pentyl.

A solution of (4R)-1-methyl-4-(prop-1-en-2-yl)cyclohex-2-en-1-ol (1 equiv) and methyl 2,4-dihydroxy-6-pentylbenzoate (1 equiv) or methyl 2,4-dihydroxy-6-propylbenzoate (1 equiv) in chlorobenzene (0.1 M) at room temperature was treated with BF3.OEt₂ (0.15 equiv) in chlorobenzene (0.05 M). The solution was stirred for 1 h then treated with aqueous NaHCO₃ and extracted with DCM, dried (MgSO₄) and concentrated. The residue was subjected to flash column chromatography (silica, 0 to 10% EtOAc/Hexane gradient elution) to give a colourless oil. Yields 60-70%

Example 2C

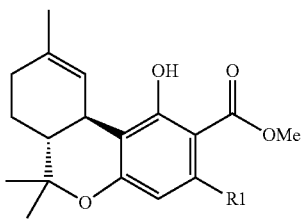

R1 is propyl or pentyl.

A solution of methyl (1'R,2'R)-2,6-dihydroxy-5'-methyl-4-pentyl-2'-(prop-1-en-2-yl)-1',2',3',4'-tetrahydro-[1,1'-biphenyl]-3-carboxylate (1 equiv) or methyl (1'R,2'R)-2,6-dihydroxy-5'-methyl-4-pentyl-2'-(prop-1-en-2-yl)-1',2',3',4'-tetrahydro-[1,1'-biphenyl]-3-carboxylate (1 equiv) in DCM (0.1 M) at −20° C. was treated with BF3.OEt₂ (0.1 equiv) in DCM (0.05 M) and stirred for 1 h as it slowly warmed to 0° C. NaHCO₃ in water was added and the aqueous phase extracted with DCM, dried (MgSO₄) and concentrated. The residue was subjected to flash column chromatography (silica, 0 to 5% EtOAc/Hexane gradient elution) to give a colourless oil. Yields 50-55%

Example 2D

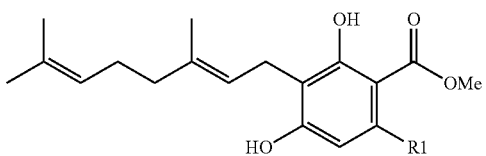

R1 is propyl or pentyl.

A solution of geraniol (1 equiv) and methyl 2,4-dihydroxy-6-pentylbenzoate (3 equiv) or methyl 2,4-dihydroxy-6-propylbenzoate (3 equiv) in CHC₃ (0.1 M) at −20° C. was treated with BF₃.OEt₂ (0.1 equiv) in CHCl₃ (0.1 M) and stirred for 0.25 h. Water was added followed and extracted with DCM, dried (MgSO₄) and concentrated. The residue was subjected to flash column chromatography (silica, 0 to 5% EtOAc/Hexane gradient elution) to give a colourless oil. Yields 30-40%.

Example 2E

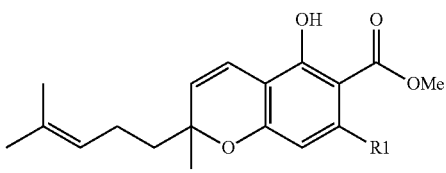

R1 is propyl or pentyl.

A solution of citral (3 equiv), 2,4-dihydroxy-6-pentylbenzoate (1 equiv) or methyl 2,4-dihydroxy-6-propylbenzoate (1 equiv) and Ca(OH)₂ (1 equiv) in methanol (0.5 M) in a sealed tube was heated at 140° C. for 1.5 h. The cooled solution was diluted with EtOAc and 1 M HCl. The separated aqueous phase was extracted with EtOAc and the combined organic layers were dried (MgSO₄) and concentrated. The residue was subjected to flash column chromatography (silica, 30% DCM/Hexane elution) to give a colourless oil. Yields 75-85%.

Example 2F

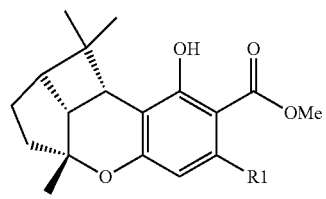

R1 is propyl or pentyl.

Example 3—Decarboxylation of Compounds of Formula I to Form Compound of Formula II According to Reaction Scheme II Reaction scheme II

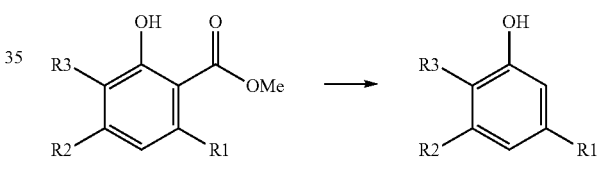

A solution of the methyl ester (1 equiv) in DMSO/water (19:1) (0.2 M) was treated with LiCl (2 equiv) and stirred at reflux for 4 h. The cooled solution was diluted with water and extracted with Et₂O (3 times). The combined organic phases were dried (MgSO₄) and concentrated and the residue was subjected to flash column chromatography (silica, 0 to 5% EtOAc/Hexane gradient elution) to give the desired decarboxylated product. Yields 80-90%.

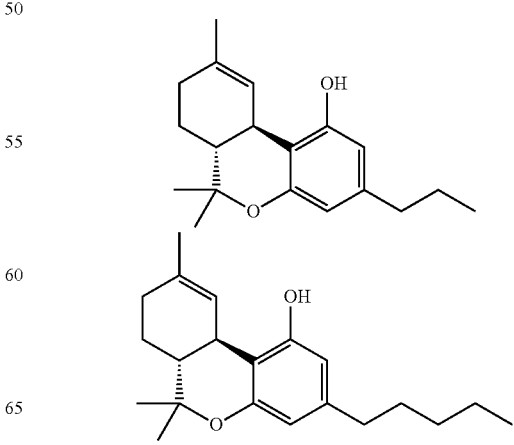

-continued

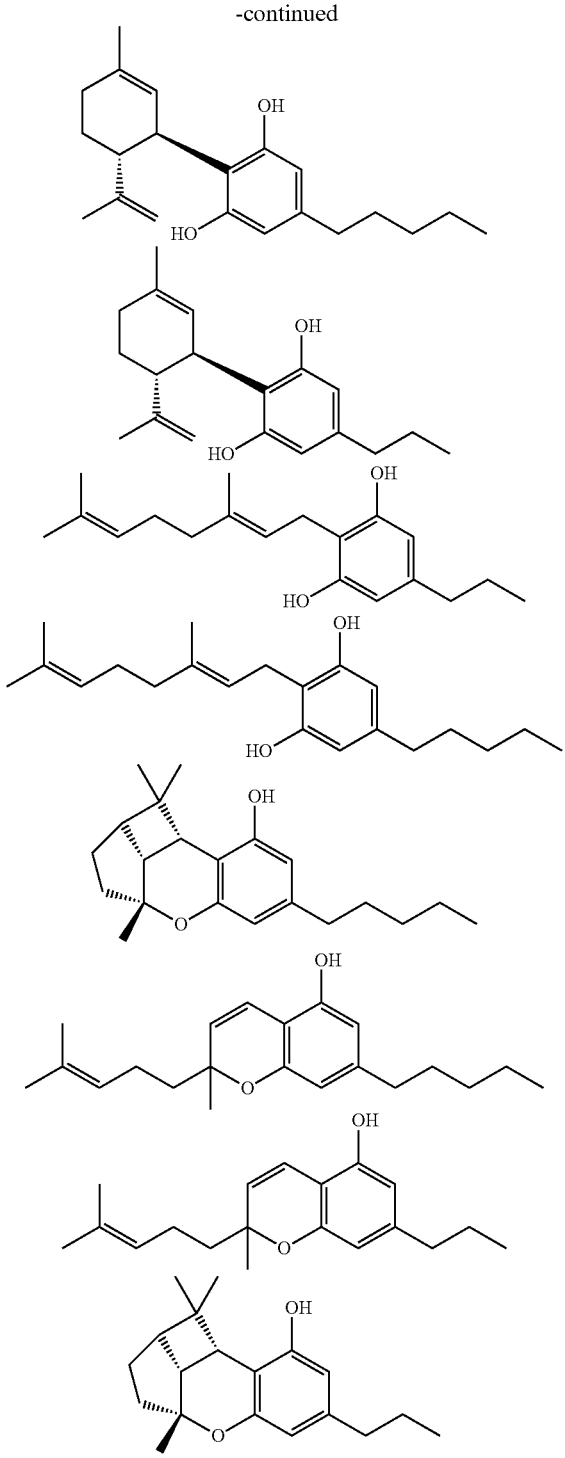

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for decarboxylating a carboxylated phytocannabinoid compound of Formula I to form a phytocannabinoid compound of Formula II:

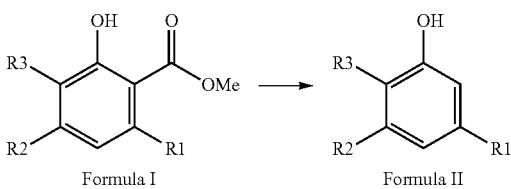

wherein:
R1 is selected from the group consisting of: substituted or unsubstituted $C_1$-$C_5$ alkyl;
R2 is selected from the group consisting of: OH or O, and R3 is selected from the group consisting of: a substituted or unsubstituted cyclohexene, a substituted or unsubstituted $C_2$-$C_8$ alkene, or a substituted or unsubstituted $C_2$-$C_8$ dialkene; or R2 is O, and R2 and R3 together form a ring structure in which R2 is an internal ring atom;
wherein the method includes heating a reaction mixture comprising the carboxylated phytocannabinoid compound and a polar aprotic solvent in the presence of a LiCl for a time sufficient to decarboxylate at least a portion of the carboxylated phytocannabinoid compounds and form the phytocannabinoid compound.

2. A method for the preparation of a phytocannabinoid compound of Formula II comprising:
subjecting a first reaction mixture comprising a compound of Formula A and a compound of Formula B in a solvent to reaction conditions such that the compound of Formula A and Formula B together undergo a condensation reaction according to Reaction Scheme I to form a carboxylated phytocannabinoid compound of Formula I:

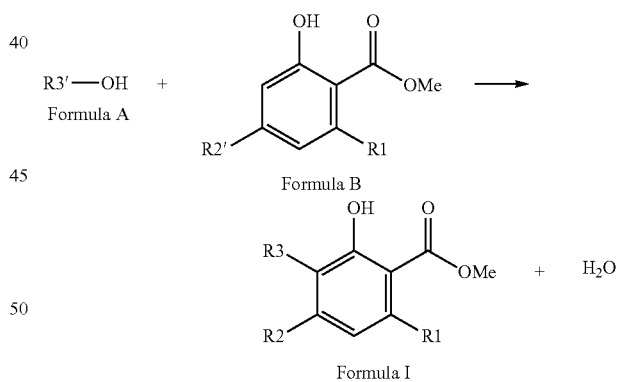

wherein:
R1 is selected from the group consisting of: unsubstituted $C_1$-$C_5$ alkyl;
R2' is OH
R3' is selected from the group consisting of: a substituted or unsubstituted cyclohexene, a substituted or unsubstituted $C_2$-$C_8$ alkene, or a substituted or unsubstituted $C_2$-$C_8$ dialkene
R2 is R2' and R3 is R3'; or R2 is O and R2 and R3 together form a ring structure in which R2 is an internal ring atom
wherein the method further includes heating a second reaction mixture comprising the carboxylated phytocannabinoid compound and a polar aprotic solvent in the presence of LiCl for a time sufficient to decarboxylate at least a portion of the carboxylated phytocannabinoid compounds and form the phytocannabinoid compound according to Reaction Scheme II;

Reaction Scheme II

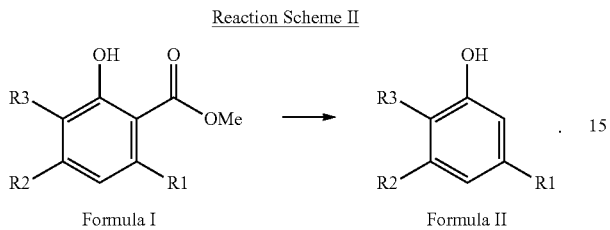

Formula I    Formula II

3. The method of claim 1, wherein, the carboxylated phytocannabinoid compound is a compound of Formula IA and the phytocannabinoid compound is a compound of Formula IIA:

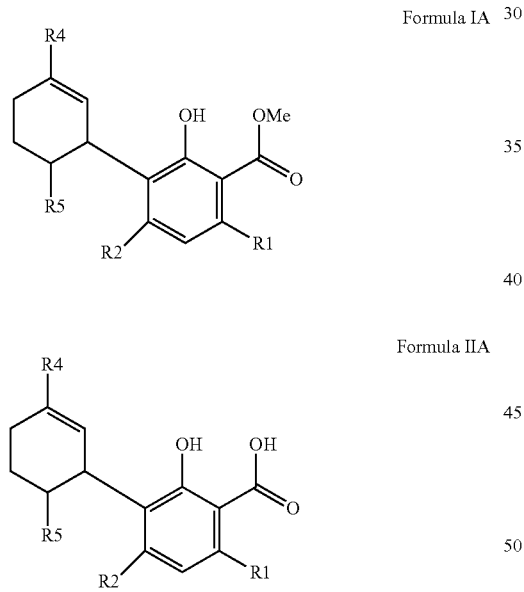

Formula IA

Formula IIA wherein:
R2 is OH and R5 is $C(CH_3)=CH_2$, or R2 is O and R5 is $C(CH_2)_2$ and R2 and R5 are linked by a covalent bond; and R4 is selected from the group consisting of: substituted or unsubstituted $C_1$-$C_4$ alkyl, COOH, COO$C_1$-$C_4$ alkyl, O$C_1$-$C_4$ alkyl, CO$C_1$-$C_4$ alkyl, tetrahydropyran, benzyl, para-methoxybenzyl, and OH.

4. The method of claim 3, wherein the carboxylated phytocannabinoid compound is a compound of Formula IB and the phytocannabinoid compound is a compound of Formula IIB:

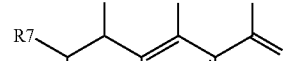

Formula IB

Formula IIB

5. The method of claim 1, wherein the carboxylated phytocannabinoid compound is a compound of Formula IC and the phytocannabinoid compound is a compound of Formula IIC:

Formula IC

Formula IIC wherein:
R6 and R7 together form a fused ring structure; R7 and R8 together form a fused ring structure; or R6, R7, and R8 together form a fused ring structure.

6. The method of claim 3, wherein the carboxylated phytocannabinoid compound is a compound of Formula ID and the phytocannabinoid compound is a compound of Formula IID:

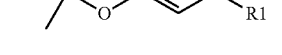

Formula ID

Formula IID

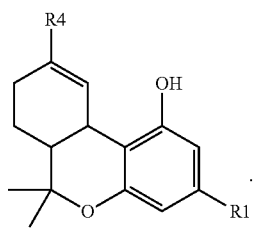

7. The method of claim 1, wherein the carboxylated phytocannabinoid compound is a compound of Formula IE and the phytocannabinoid compound is a compound of Formula IIE:

Formula IE

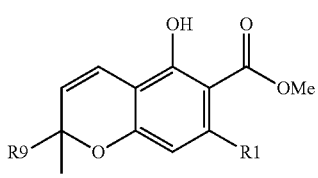

Formula IIE

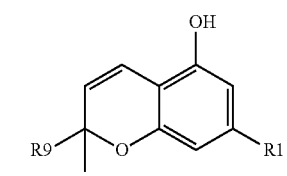

wherein:
R9 is selected from the group consisting of: a substituted or unsubstituted $C_2$-$C_8$ alkene, or a substituted or unsubstituted $C_2$-$C_8$ dialkene.

8. The method of claim 2, wherein the first reaction mixture further comprises $BF_3 \cdot OEt_2$.

9. The method of claim 1, wherein the polar aprotic solvent is selected from the group consisting of: N-methylpyrrolidone, tetrahydrofuran (THF), ethyl acetate (EtOAc), acetone, dimethylformamide (DMF), acetonitrile (MeCN), dimethyl sulfoxide (DMSO), propylene carbonate (PC), and combinations thereof.

10. The method of claim 1, wherein the phytocannabinoid compound is selected from the group consisting of:

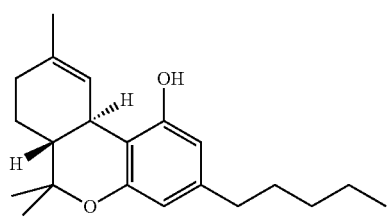 [SMILES: CCCCCc1cc(O)c2c(c1)OC(C)(C)[C@@H]1CCC(C)=C[C@@H]21]

Tetrahydrocannabinol (THC)
(6aR,10aR)-6,6,9-trimethyl-3-pentyl-6a,7,8,10a-tetrahydro-6H-benzo[c]chromen-1-ol

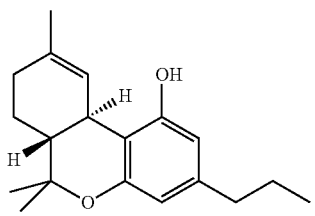 [SMILES: CCCc1cc(O)c2c(c1)OC(C)(C)[C@@H]1CCC(C)=C[C@@H]21]

Tetrahydrocannabivarin (THCV)
(6aR,10aR)-6,6,9-trimethyl-3-propyl-6a,7,8,10a-tetrahydro-6H-benzo[c]chromen-1-ol

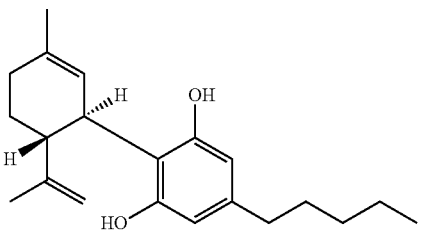 [SMILES: C=C(C)[C@@H]1CCC(C)=C[C@H]1c1c(O)cc(CCCCC)cc1O]

Cannabidiol (CBD)
(1'R,2'R)-5'-methyl-4-pentyl-2'-(prop-1-en-2-yl)-1',2',3',4'-tetrahydro-[1,1'-biphenyl]-2,6-diol

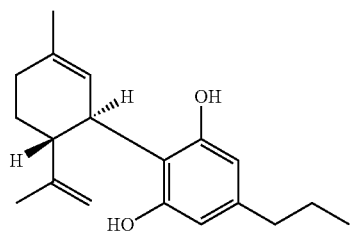 [SMILES: C=C(C)[C@@H]1CCC(C)=C[C@H]1c1c(O)cc(CCC)cc1O]

Cannabidivarin (CBDV)
(1'R,2'R)-5'-methyl-2'-(prop-1-en-2-yl)-4-propyl-1',2',3',4'-tetrahydro-[1,1'-biphenyl]-2,6-diol

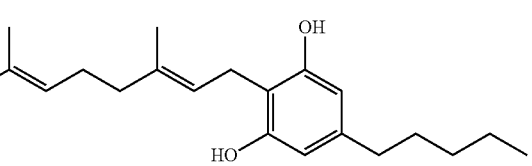

Cannabigerol (CBG)
(E)-2-(3,7-dimethylocta-2,6-dien-1-yl)-5-pentylbenzene-1,3-diol

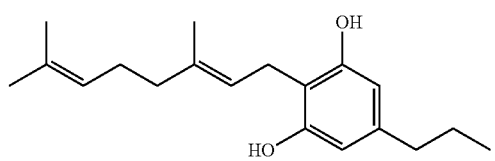 [SMILES: CCCc1cc(O)c(C/C=C(\C)CCC=C(C)C)c(O)c1]

Cannabigerovarin (CBGV)
(E)-2-(3,7-dimethylocta-2,6-dien-1-yl)-5-propylbenzene-1,3-diol

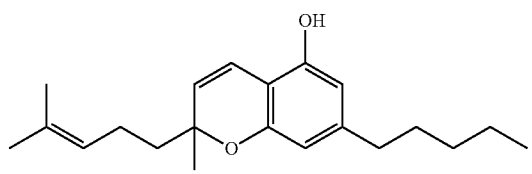 [SMILES: CCCCCc1cc(O)c2c(c1)OC(C)(CCC=C(C)C)C=C2]

Cannabichromene (CBC)
2-methyl-2-(4-methylpent-3-en-1-yl)-7-pentyl-2H-chromen-5-ol

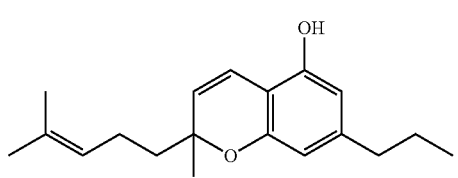 [SMILES: CCCc1cc(O)c2c(c1)OC(C)(CCC=C(C)C)C=C2]

Cannabichromevarin (CBCV)
2-methyl-2-(4-methylpent-3-en-1-yl)-7-propyl-2H-chromen-5-ol

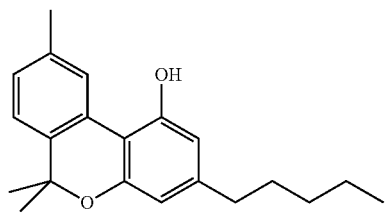 [SMILES: CCCCCc1cc(O)c2c(c1)OC(C)(C)c1ccc(C)cc1-2]

Cannabinol (CBN)
6,6,9-trimethyl-3-pentyl-6H-benzo[c]chromen-1-ol

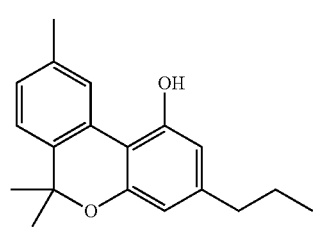 [SMILES: CCCc1cc(O)c2c(c1)OC(C)(C)c1ccc(C)cc1-2]

Cannabinovarin (CBNV)
6,6,9-trimethyl-3-propyl-6H-benzo[c]chromen-1-ol

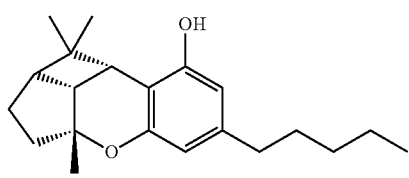

Cannabicyclol (CBL)
(1aS,1a$^1$R,3aR,8bR)-1,1,3a-trimethyl-6-pentyl-1a,1a$^1$,2,3,3a,8b-hexahydro-1H-4-oxabenzo[f]cyclobuta[cd]inden-8-ol

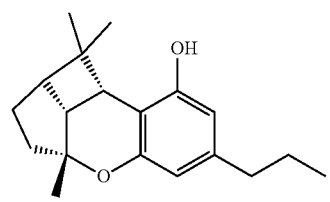

Cannabicyclovarin (CBLV)
(1aS,1a$^1$R,3aR,8bR)-1,1,3a-trimethyl-6-propyl-1a,1a$^1$,2,3,3a,8b-hexahydro-1H-4-oxabenzo[f]cyclobuta[cd]inden-8-ol

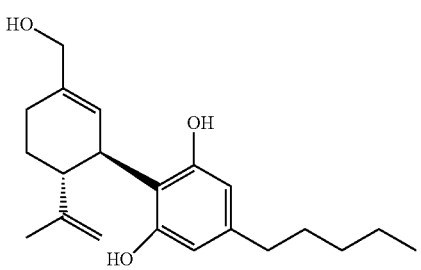 [SMILES: C=C(C)[C@@H]1CCC(CO)=C[C@H]1c1c(O)cc(CCCCC)cc1O]

11-Hydroxycannabidiol (11-OH—CBD)
(1'R,2'R)-5'-(hydroxymethyl)-4-pentyl-2'-(prop-1-en-2-yl)-1',2',3',4'-tetrahydro-[1,1'-biphenyl]-2,6-diol

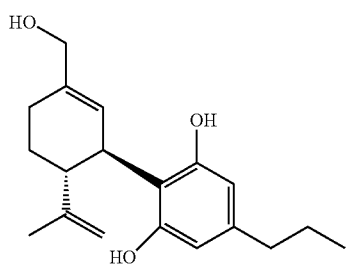 [SMILES: C=C(C)[C@@H]1CCC(CO)=C[C@H]1c1c(O)cc(CCC)cc1O]

11-Hydroxycannabidivarin (11-OH—CBDV)
(1'R,2'R)-5'-(hydroxymethyl)-2'-(prop-1-en-2-yl)-4-propyl-1',2',3',4'-tetrahydro-[1,1'-biphenyl]-2,6-diol

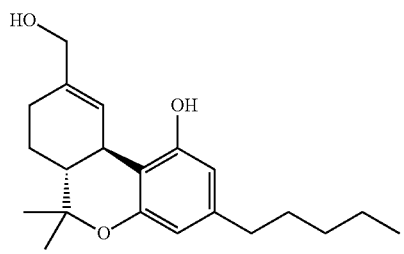 [SMILES: CCCCCc1cc(O)c2c(c1)OC(C)(C)[C@@H]1CCC(CO)=C[C@@H]21]

11-Hydroxytetrahydrocannabinol (11-OH—THC)
(6aR,10aR)-9-(hydroxymethyl)-6,6-dimethyl-3-pentyl-6a,7,8,10a-tetrahydro-6H-benzo[c]chromen-1-ol

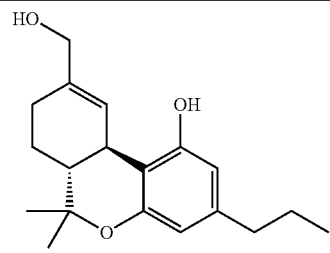

11-Hydroxytetrahydrocannabivarin (11-OH—THCV)
(6aR,10aR)-9-(hydroxymethyl)-6,6-dimethyl-3-
propyl-6a,7,8,10a-tetrahydro-6H-benzo[c]chromen-
1-ol

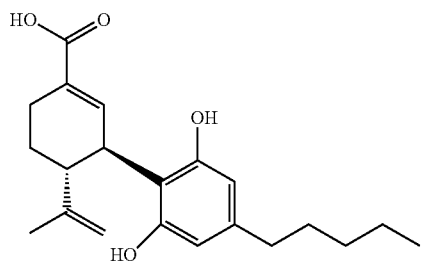 [SMILES: C=C(C)[C@@H]1CCC(C(=O)O)=C[C@H]1c1c(O)cc(CCCCC)cc1O]

11-Carboxycannabidiol (11-COOH—CBD)
(1R,6R)-2',6'-dihydroxy-4'-pentyl-6-(prop-1-en-2-yl)-
1,4,5,6-tetrahydro-[1,1'-biphenyl]-3-carboxylic acid

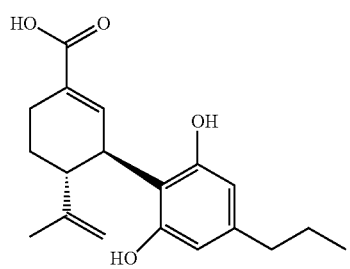 [SMILES: C=C(C)[C@@H]1CCC(C(=O)O)=C[C@H]1c1c(O)cc(CCC)cc1O]

11-Carboxycannabidivarin (11-COOH—CBDV)
(1R,6R)-2',6'-dihydroxy-6-(prop-1-en-2-yl)-4'-propyl-
1,4,5,6-tetrahydro[1,1'-biphenyl]-3-carboxylic acid

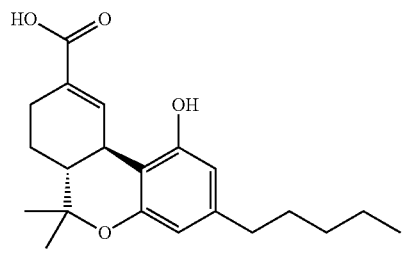 [SMILES: CCCCCc1cc(O)c2c(c1)OC(C)(C)[C@@H]1CCC(C(=O)O)=C[C@@H]21]

11-Carboxytrahydrocannabinol (11-COOH—THC)
(6aR,10aR)-1-hydroxy-6,6-dimethyl-3-pentyl-
6a,7,8,10a-tetrahydro-6H-benzo[c]chromene-9-
carboxylic acid

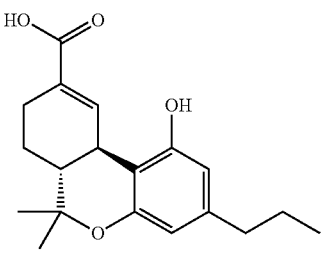 [SMILES: CCCc1cc(O)c2c(c1)OC(C)(C)[C@@H]1CCC(C(=O)O)=C[C@@H]21]

11-Carboxytrahydrocannabivarin(11-COOH—THCV)
(6aR,10aR)-1-hydroxy-6,6-dimethyl-3-propyl-
6a,7,8,10a-tetrahydro-6H-benzo[c]chromene-9-
carboxylic acid.

11. The method of claim 1, wherein the step of heating the reaction mixture includes heating the reaction mixture to the boiling point of the polar aprotic solvent.

12. The method of claim 11, wherein the step of heating the reaction mixture is conducted under reflux.

13. The method of claim 1, wherein the LiCl is present in an amount of from 1 to 3 molar equivalents relative to the compound of Formula I.

14. The method of claim 13, wherein the LiCl is present in an amount of from about 1.5 to about 2.5 molar equivalents.

15. The method of claim 14, wherein the LiCl is present in an amount of about 2 molar equivalents.

16. The method of claim 1, wherein the polar aprotic solvent has a boiling point that is above 100° C.

17. The method of claim 16, wherein the polar aprotic solvent has a boiling point that is above 130° C.

* * * * *